US007884167B2

United States Patent
(12) United States Patent
Nakanishi et al.

(10) Patent No.: US 7,884,167 B2
(45) Date of Patent: Feb. 8, 2011

(54) METHOD FOR PRODUCTION OF POLYFUNCTIONAL COMPOUND

(75) Inventors: Sadahrio Nakanishi, Osaka (JP); Mitsuru Ueda, Tokyo (JP)

(73) Assignee: Nitto Denko Corporation, Ibaraki-shi, Osaka (JP)

( * ) Notice: Subject to any disclaimer, the term of this patent is extended or adjusted under 35 U.S.C. 154(b) by 0 days.

(21) Appl. No.: 12/306,490

(22) PCT Filed: Jul. 4, 2007

(86) PCT No.: PCT/JP2007/063344

§ 371 (c)(1), (2), (4) Date: Dec. 23, 2008

(87) PCT Pub. No.: WO2008/007589

PCT Pub. Date: Jan. 17, 2008

(65) Prior Publication Data

US 2009/0182107 A1 Jul. 16, 2009

(30) Foreign Application Priority Data

Jul. 11, 2006 (JP) ............................ 2006-190186

(51) Int. Cl.

*C08F 226/02* (2006.01)
*C08F 118/02* (2006.01)
*C08F 120/18* (2006.01)
*C08F 20/56* (2006.01)

(52) U.S. Cl. ................ 526/307.6; 526/319; 526/329.7; 525/329.4

(58) Field of Classification Search ............. 526/307.6, 526/319, 329.7; 525/329.4

See application file for complete search history.

(56) References Cited

U.S. PATENT DOCUMENTS

| | | | |
|---|---|---|---|
| 6,103,323 | A | 8/2000 | Motomura et al. |
| 6,423,799 | B1 | 7/2002 | Berneth et al. |

FOREIGN PATENT DOCUMENTS

| | | | | |
|---|---|---|---|---|
| CA | 2366846 | A1 | | 9/2000 |
| JP | 09-133810 | A | | 5/1997 |
| JP | 2000-514468 | A | | 10/2000 |
| JP | 2001-172385 | A | | 6/2001 |
| JP | 2002-167370 | A | | 6/2002 |
| JP | 2002167370 | A | * | 6/2002 |
| JP | 2002-539476 | A | | 11/2002 |
| JP | 2003-226682 | A | | 8/2003 |
| JP | 2003226682 | A | * | 8/2003 |
| JP | 2006-219383 | A | | 8/2006 |
| JP | 2006219383 | A | * | 8/2006 |

* cited by examiner

*Primary Examiner*—Michael M Bernshteyn
(74) *Attorney, Agent, or Firm*—Westerman, Hattori, Daniels & Adrian, LLP

(57) ABSTRACT

Provided is an easy method for production of a high-performance polyfunctional compound which can be used as an optical recording material, an optical waveguide material, a photo-alignment film material, or the like, in a simple manner. The method for production of a polyfunctional compound includes conducting a Michael addition of a compound (A) having a hydrogen atom of pKa≦15 to a (meth)acrylate or a (meth)acrylamide (B), in which at least one of the compounds (A) and (B) has a photoisomerization group and/or a liquid-crystalline group.

9 Claims, No Drawings

METHOD FOR PRODUCTION OF POLYFUNCTIONAL COMPOUND

TECHNICAL FIELD

The present invention relates to a method for production of a polyfunctional compound. More specifically, the present invention relates to an easy method for production of a high-performance polyfunctional compound, which can be used as an optical recording material, an optical waveguide material, a photo-alignment film material, or the like.

As a hologram recording material which does not require an external electric field, an organic material having an azobenzene skeleton is known. In hologram recording, the photoisomerization reaction of an azobenzene skeleton plays an important role. When a film using such a material is irradiated with linearly polarized light, the azobenzene skeleton is realigned due to the isomerization cycle of trans-cis-trans.

The azobenzene skeleton absorbs light corresponding to a p-p* transition, and is excited from a thermally stable trans form to a cis form to cause the modulation of a refractive index. The cis form generated by photoexcitation returns to a trans form spontaneously due to thermal relaxation. Therefore, when natural light is used as a light source, a large modulation of a refractive index cannot be expected. However, the following is known. When polarized light is used as a light source, only a trans form azobenzene skeleton having an electric field matched with an electric vector of polarized light is excited, and further, when the excited cis form azobenzene skeleton returns to a trans form due to thermal relaxation, the excited cis form azobenzene skeleton returns to a trans form having an electric field perpendicular to the electric vector of polarized light. Thus, the azobenzene skeleton that cannot be excited is accumulated in the light-irradiated part to cause birefringence, and the modulation of a refractive index due to the birefringence is caused (Weigert effect: for example, see Next-generation polymer/supermolecule controlling light, NTS (2000) edited by The Society of Polymer Science, Japan). Further, when a light-irradiated site is heated or the like, the light-irradiated site changes to a trans form having random alignment (electric field) in an initial state to eliminate birefringence due to the molecular movement, whereby data can be written again. Due to the change in alignment, photoisomerization, i.e., birefringence and dichroism are induced, whereby hologram recording can be performed. Thus, an organic material having an azobenzene skeleton has a potential for a rewritable optical recording material, and in particular, for a hologram recording material.

As such a hologram recording material, a hologram recording material using a (meth) acrylic polymer having a photoisomerization group with a particular structure at a side chain (for example, see Patent Documents 1 and 2).

On the other hand, a polymer containing a side-chain liquid-crystalline group has an anisotropic property. Therefore, a number of examples of applications to optical uses such as a liquid crystal display have been reported. The side-chain type liquid crystal polymer is used as an optical element such as a viewing angle compensation film, a retardation film, and a cholesteric reflection film, using a birefringence phenomenon of the side-chain type liquid crystal polymer (for example, see Patent Document 3).

A typical specific examples of the polymer containing a side-chain type liquid-crystalline group includes a (meth) acrylic polymer containing a side-chain type liquid-crystalline group.

The above-mentioned side-chain type polymer containing a functional group such as a photoisomerization group or a liquid-crystalline group can be produced by a method such as polymerization of functional monomers, and molecular weights thereof can be controlled to some degree depending upon the polymerization conditions. However, the polymer containing a side-chain type functional group is present as a mixture containing components of a plurality of molecular weights, and hence the molecular weights have a distribution. Thus, the polymer containing a side-chain functional group has problems in compatibility and solubility in the case of producing an optical element using the polymer containing a side-chain functional group.

Due to the above points, there is a demand for a method for easy production of a polymer containing a functional group in which the molecular weight distribution is as close to 1 as possible.

Further, in general, the polymer containing a functional group such as a liquid crystal polymer is poor in compatibility with other components. Therefore, for example, in order to combine functional sites such as a liquid-crystalline group, a cross-linking group, and a chiral group, the polymer containing a functional group needs to be subjected to a synthesis operation such as copolymerization, which makes a production process complicated.

As a method of obtaining a liquid crystal compound excellent in compatibility with other components, the concept of vitrified liquid crystal has been reported recently.

The liquid crystal compound expressing such a concept has a plurality of liquid-crystalline groups at ends and also has a configuration in which a liquid-crystalline group and a core portion are connected via a connecting group. Due to such a configuration, the enhancement of compatibility to some degree and the enhancement of uniform coating performance are recognized.

Patent Document 1: JP 2000-514468 A

Patent Document 2: JP 2002-539476 A

Patent Document 3: JP 09-133810 A

DISCLOSURE OF THE INVENTION

Problems to be Solved by the Invention

The present invention has been made in view of solving the conventional problems as described above, and an object of the present invention is to provide a method for easy production of a high-performance polyfunctional compound which can be used as an optical recording material, an optical waveguide material, a photo-alignment film material, or the like.

Means for Solving the Problems

A method for production of a polyfunctional compound according to the present invention includes conducting a Michael addition of a compound (A) having a hydrogen atom of pKa≦15 to a (meth)acrylate or a (meth)acrylamide (B), in which at least one of the compounds (A) and (B) has a photoisomerization group.

Another method for production of a polyfunctional compound according to the present invention includes conducting a Michael addition of a compound (A) having a hydrogen atom of pKa≦15 to a (meth)acrylate or a (meth)acrylamide (B), in which at least one of the compounds (A) and (B) has a liquid-crystalline group.

Still another method for production of a polyfunctional compound according to the present invention includes conducting a Michael addition of a compound (A) having a hydrogen atom of pKa≦15 to a (meth)acrylate or a (meth) acrylamide (B), in which at least one of the compounds (A) and (B) has both a photoisomerization group and a liquid-crystalline group.

In a preferred embodiment of the method for production of a polyfunctional compound according to the present invention, the compound (A) includes at least one selected from cyanoacetates, acetoacetates, malonates, and 1,3-acetone-dicarboxylic acid diesters.

In a preferred embodiment of the method for production of a polyfunctional compound according to the present invention, the compound (A) includes cyanoacetates.

In a preferred embodiment of the method for production of a polyfunctional compound according to the present invention, the Michael addition is performed using a hydrogen-abstraction catalyst.

In a preferred embodiment of the method for production of a polyfunctional compound according to the present invention, the hydrogen-abstraction catalyst includes a base catalyst.

In a preferred embodiment of the method for production of a polyfunctional compound according to the present invention, the hydrogen-abstraction catalyst includes an amine-based catalyst.

In a preferred embodiment of the method for production of a polyfunctional compound according to the present invention, the photoisomerization group has a structure represented by General Formula (2):

(2)

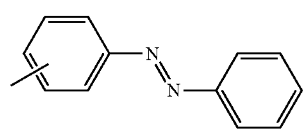

where: each aromatic ring may have one or more substituents.

In a preferred embodiment of the method for production of a polyfunctional compound according to the present invention, the liquid-crystalline group has a structure represented by any of General Formulae (3a) to (3g):

$$—C_y—C_y \quad (3a)$$

$$—C_y—C_y—C_y \quad (3b)$$

$$—C_y—Y—C_y \quad (3c)$$

$$—C_y—Y—C_y—Y—C_y \quad (3d)$$

$$—C_y—C{\equiv}C—C_y \quad (3e)$$

$$—C_y—C{\equiv}C—C_y—C{\equiv}C—C_y \quad (3f)$$

$$—C_y—Y—C_y—C{\equiv}C—C_y \quad (3g)$$

where: Y's represent any of —COO—, —OCO—, —CONH—, CON(alkyl)-, and —CH═N—; and Cy's each independently represent a phenyl ring, a naphthyl ring, a biphenyl ring, and a cyclohexyl ring which may have at least one substituent selected from F, CN, an alkoxy group, and an alkyl group.

In a preferred embodiment of the method for production of a polyfunctional compound according to the present invention, the polyfunctional compound to be obtained has a molecular weight of 500 to 5,000.

Effects of the Invention

According to the present invention, a method for easy production of a polyfunctional compound that can be used as an optical recording material on which a large quantity of data information can be recorded optically at a high density, which can be used as an optical waveguide material using a refractive index difference occurring between a light-irradiated part and a part not irradiated with light, and which is capable of forming a film and can be used as a photo-alignment film material having excellent photosensitivity.

BEST MODE FOR CARRYING OUT THE INVENTION

Hereinafter, preferred embodiments of the present invention will be described, but the present invention is not limited to those embodiments. In the specification of the present invention, "(meth)acrylic acid" refers to acrylic acid or methacrylic acid.

<<Method for Production of a Polyfunctional Compound>>

In the production method of the present invention, a polyfunctional compound is produced by conducting a Michael-addition of a compound (A) having a hydrogen atom of pKa≦15 to a (meth)acrylate or (meth) acry amide (B). The compounds (A) and (B) may be used alone or in a mixture.

As the compound (A), any suitable compound can be selected as long as the compound has a hydrogen atom of pKa≦15. In order for the compound to have a hydrogen atom of pKa≦15, it is preferred that the compound have active methylene and, for example, it is preferred that the compound have carbon sandwiched between two electron withdrawing groups. Specific examples include cyanoacetates, acetoacetates, malonates, and 1,3-acetone-dicarboxylic acid diesters. Cyanoacetates are preferred.

The compound (A) is deprotonated easily by the stabilization effect of carboanions generated on carbon of active methylene to generate anions. For example, the pKa value of hydrogen on carbon at a position adjacent to ketone at which only one adjacent carbonyl group is present is about 20, whereas the pKa value of carbon sandwiched between two ester groups of a malonic acid diester is about 10 to about 13. Thus, the acidity changes remarkably. Therefore, the malonic acid diester can generate carboanions easily in the presence of an amine-based catalyst and a base catalyst having basicity to such a degree as that of alkoxide. The generated carboanions function as active nucleophiles, and can be subjected to a Michael addition reaction with (meth)acrylates which are unsaturated carbonyl compounds.

In the Michael addition reaction of the compound (A) and compound (B), as long as the pKa in the active hydrogen of the compound (A) is 15 or less, the reaction efficiently progresses. Examples thereof may include 1,3-cyclohexanedione (pKa=4.8), malonaldehyde (pKa=5.0), meldrum acid (pKa=5.1), 2,4-pentanedione (pKa=8.9), malononitrile (pKa=11.0), acetoacetate (pKa=11.0), bis(methylsulfonyl) methane (pKa=12.7), cyanoacetate (pKa=13.1), and malonate (pKa=13.5). From the viewpoint of versatility of the raw material, cyanoacetates, malonates, and acetoacetates are preferable. Active methylene compounds including 1,3-acetone dicarboxylic acid diester, a cyanoacetate group, a malonate group, an acetoacetate group may also be used as active methylene compounds.

The compound (A) preferably contains a photoisomerization group and/or a liquid-crystalline group.

As the photoisomerization group which the compound (A) may have, any suitable photoisomerization group can be selected as long as a photoisomerization site causes an isomerization reaction by light irradiation. In the present invention, a photoisomerization group having a structure represented by General Formula (2) is preferred.

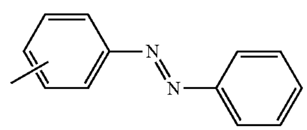

(2)

In General Formula (2), each aromatic ring may have one or more substituents. Further, at last two substituents of each aromatic ring may be connected to form a new ring structure.

As the liquid-crystalline group which the compound (A) may have, any suitable liquid-crystalline group can be selected. In the present invention, a liquid-crystalline group having a structure represented by any of General Formulae (3a) to (3g) is preferred.

$$—C_y—C_y \qquad (3a)$$

$$—C_y—C_y—C_y \qquad (3b)$$

$$—C_y—Y—C_y \qquad (3c)$$

$$—C_y—Y—C_y—Y—C_y \qquad (3d)$$

$$—C_y—C{\equiv}C—C_y \qquad (3e)$$

$$—C_y—C{\equiv}C—C_y—C{\equiv}C—C_y \qquad (3f)$$

$$—C_y—Y—C_y—C{\equiv}C—C_y \qquad (3g)$$

In General Formulae (3a) to (3g): Y's represent any of —COO—, —OCO—, —CONH—, CON (alkyl)-, and —CH═N—; and Cy's each independently represent a phenyl ring, a naphthyl ring, a biphenyl ring, and a cyclohexyl ring which may have at least one substituent selected from F, CN, an alkoxy group, and an alkyl group.

The compound (B) is a (meth)acrylate or (meth)acrylamide. As the (meth)acrylate, any suitable (meth)acrylate can be selected. As the (meth)acrylamide, any suitable (meth) acrylamide can be selected.

It is preferred that the compound (B) have a photoisomerization group and/or a liquid-crystalline group.

The photoisomerization groups which the compound (B) may have are similar to those which the compound (A) may have.

The liquid-crystalline groups which the compound (B) may have are similar to those which the compound (A) can have.

In the production method of the present invention, the Michael addition reaction is preferably performed by using hydrogen-abstraction catalyst. Examples of the hydrogen-abstraction catalyst include, as amine-based catalysts, basic ionic liquids such as imidazoline, proline, quinaalkaloid, triazabicyclodecene (TBD), diazabicyclo undecene (DBU), hexahydromethyl pyrimidopyrimidine (MTBD), diazabicyclo nonane (DBN), tetramethyl guanidine (TMG), diazabicyclooctane (DABCO), diisopropyl ethylamine (DIPEA), tetramethyl piperadine (TMP), catalysts in which TBD is carried on a solid-phase such as cross-linked polystyrene or silica gel, and butylmethylimidazolium hydroxide. Further, examples of the base catalyst may include: quaternary ammonium hydroxides such as sodium methoxide, sodium ethoxide, potassium tertiary butoxide, potassium hydroxide, sodium hydroxide, and tetramethyl ammonium hydroxide; sodium metal; lithium diisopropyl amide (LDA); and butyl lithium. Further, organic metal catalysts include: ruthenium-based catalysts such as ruthenium cyclooctadiene cyclooctatriene and hydridoruthenium; iron-based catalysts such as trichloride iron and iron acetylacetonate; nickel-based catalysts such as nickel acetyl acetonate, nickel acetate, and nickel salicyl aldehyde; copper-based catalysts; parridium-based catalysts; scandium-based catalysts; lanthanum-based catalysts; and ytterbium-based catalysts. Of those, from the viewpoint of low amounts of side reactions and staining, and versatility of reagent, amine-based catalysts and base catalysts are preferable, and triazabicyclodecene (TBD), diazabicyclo undecene (DBU), and potassium tertiary butoxide are particularly preferably used. Further, in the case of using, although not a general-purpose reagent, a catalyst (product manufactured by Argonaut) in which TBD is carried on a solid phase such as cross-linked polystyrene or silica gel, the catalyst can be removed easily by filtering a reaction solution after the completion of the reaction. Therefore, the purification can be performed easily, and in addition, the solution can be casted as it is without being purified by re-precipitation to form a film. Thus, such a catalyst can be used preferably from an atom economical viewpoint. The hydrogen-abstraction catalysts may be used alone or in combination.

The use amount of the hydrogen-abstraction catalyst may be a catalyst amount with respect to raw materials. When the use amount is too large, a side-reaction may be caused, and when the use amount is too small, the reaction may not proceed. The preferable use amount is 0.0001 to 100 mol %, more preferably 0.01 to 10 mol %, and still more preferably 0.1 to 10 mol %.

The reaction temperature of the Michael addition reaction is preferably −78 to 200° C., more preferably 0 to 80° C., and still more preferably around room temperature, i.e., about 25° C.

The reaction time of the Michael addition reaction is preferably 10 seconds to 1 week, more preferably 1 minute to 10 hours, and still more preferably 3 minutes to 5 hours. The reaction may be completed appropriately by checking the reaction progress by analysis means such as thin layer chromatography (TLC), NMR, and infrared spectroscopy.

As the reaction solvent to be used in the Michael addition reaction, any suitable solvent can be adopted as long as it does not react with the hydrogen-abstraction catalyst to be used, does not react with or decompose a base, and preferably dissolves a raw material compound. For example, a solvent that dissolves an intended substance due to the final increase in solubility of a polyfunctional compound may be used although a raw material compound is not completely dissolved therein. The solvent is preferably a dehydrated solvent, but the reaction can also proceed with a solvent that is not dehydrated.

<<Polyfunctional compound>>

The polyfunctional compound of the present invention preferably includes a chemical structure represented by General Formula (1).

(1)

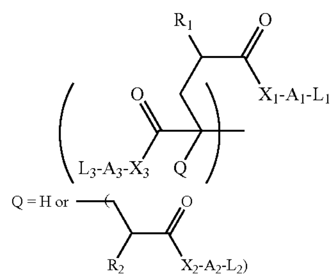

In General Formula (1), $R_1$ and $R_2$ each independently represent any of H, $CH_3$, and Cl.

In General Formula (1), $X_1$ to $X_3$ each independently represent any of —O—, —NH—, and —N(alkyl group)-.

In General Formula (1), $A_1$ to $A_3$ each independently represent a divalent connecting group. The divalent connecting group in the present invention refers to an alkylene group or a single bond having 1 to 12 carbon atoms. One —$CH_2$— present in the alkylene group or two or more —$CH_2$— which are not adjacent to each other may be replaced by —O—. Further, the alkylene group may contain a benzoate skeleton or an amide benzoate skeleton such as —O-Ph-CO—, —NH-Ph-CO—, or —N (alkyl group) Ph-CO—. Herein, Ph represents a benzene ring which may be substituted.

In General Formula (1), $L_1$ to $L_3$ each independently represent any of a photoisomerization group, a liquid-crystalline group, and H, and at least one of $L_1$ to $L_3$ represents a photoisomerization group.

As the photoisomerization group, any suitable photoisomerization group can be selected as long as a photoisomerization site causes an isomerization reaction by light irradiation. Examples of the photoisomerization group include a group having an azobenzene skeleton and a group having a stilbene skeleton, causing trans-cis isomerization. The group having an azobenzene skeleton is preferred in the present invention. Specifically, a photoisomerization group having a structure represented by General Formula (2) is preferred.

(2)

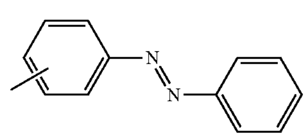

In General Formula (2), each aromatic ring may have one or more substituents. Further, at last two substituents of each aromatic ring may be connected to form a new ring structure.

As the liquid-crystalline group, any suitable liquid-crystalline group can be selected. In the present invention, a liquid-crystalline group having a structure represented by any of General Formulae (3a) to (3g) is preferred.

$$—C_y—C_y \quad (3a)$$

$$—C_y—C_y—C_y \quad (3b)$$

$$—C_y—Y—C_y \quad (3c)$$

$$—C_y—Y—C_y—Y—C_y \quad (3d)$$

$$—C_y—C{\equiv}C—C_y \quad (3e)$$

$$—C_y—C{\equiv}C—C_y—C{\equiv}C—C_y \quad (3f)$$

$$—C_y—Y—C_y—C{\equiv}C—C_y \quad (3g)$$

In General Formulae (3a) to (3g): Y's represent any of —COO—, —OCO—, —CONH—, CON(alkyl)-, and —CH═N—; and Cy's each independently represent a phenyl ring, a naphthyl ring, a biphenyl ring, and a cyclohexyl ring which may have at least one substituent selected from F, CN, an alkoxy group, and an alkyl group.

Note that, regarding a plurality of Xn-An-Ln groups (n=1 to 3) in General Formula (1), Ln is not necessarily connected to all the Xn-An-Ln groups (n=1 to 3). That is, all the carbon-hydrogen bonds of active methylene may not be substituted for carbon-carbon bonds due to the insufficient Michael reaction. More specifically, a compound may be used in which An-Ln is proton (H). Further, the entire An-Ln may be any monovalent connecting group. An may be a single bond.

One preferred embodiment of the polyfunctional compound obtained by the production method of the present invention is a polyfunctional compound represented by General Formula (1a).

(1a)

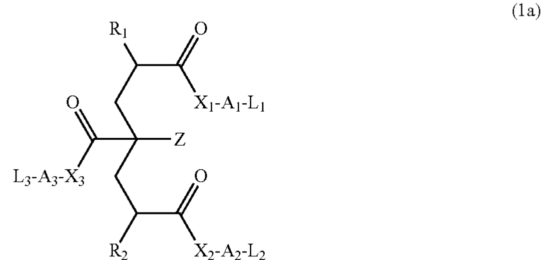

In General Formula (1a): $R_1$ and $R_2$ each independently represent any of H, $CH_3$, and Cl; Z represents any of CN and $COCH_3$; $X_1$ to $X_3$ each independently represent —O—, —NH—, and —N(alkyl group)-; $A_1$ to $A_3$ each independently represent a divalent connecting group; and $L_1$ to $L_3$ each independently represent a photoisomerization group, a liquid-crystalline group, and H, and at least one of $L_1$ to $L_3$ represents a photoisomerization group or a liquid-crystalline group.

As an example of the polyfunctional compound obtained by the production method of the present invention in which $R_1$ and $R_2$ each represent H, Z represents CN, $X_1$ to $X_3$ each represent —O—, $A_1$ to $A_3$ each represent an ethylene group in General Formula (1a), there is exemplified a polyfunctional compound having the following structure. The compound can be synthesized by coupling reaction of cyanoacetates having an azobenzene structure with acrylate having a cyanobiphenyl structure using a hydrogen-abstraction catalyst.

[Chemical Formula 9]
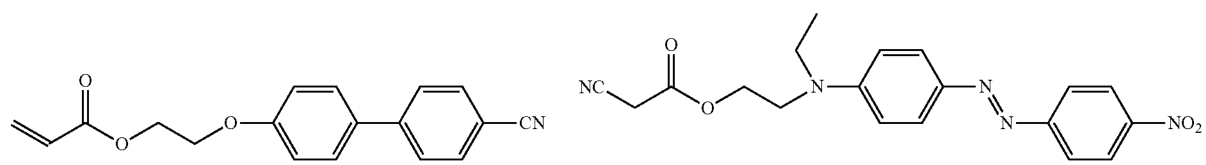
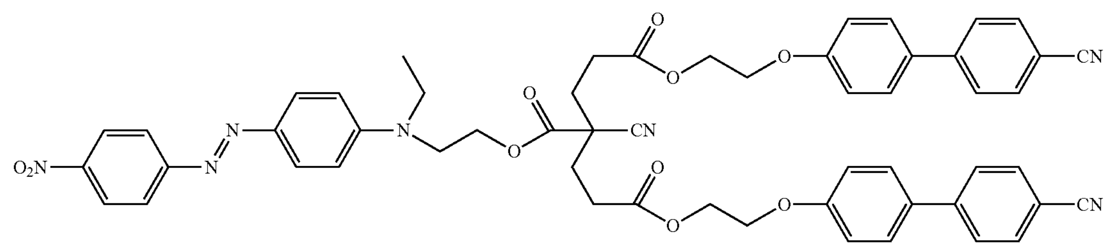
The compound in which Z represents $COCH_3$ instead of CN can be synthesized in the same way by changing cyanoacetate that is used as a material in the above to acetoacetate.
[Chemical Formula 10]
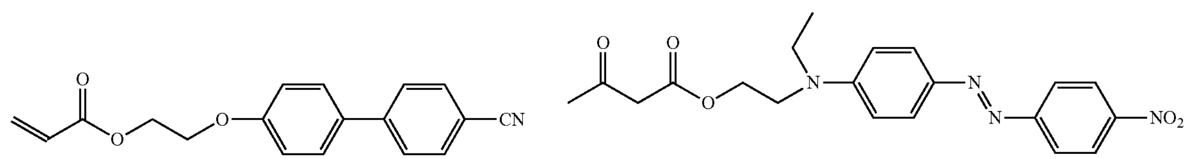
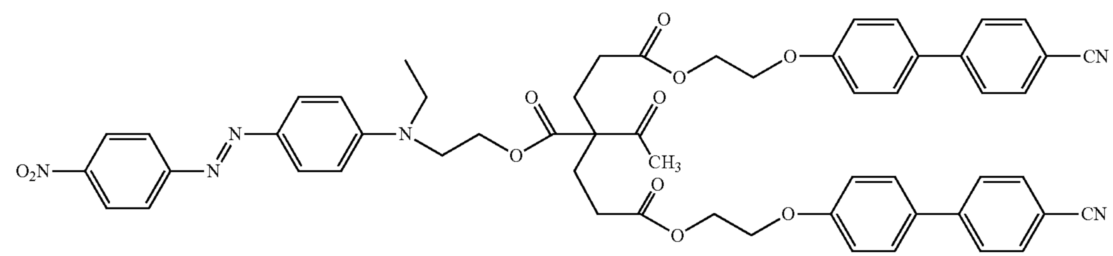

One preferred embodiment of the polyfunctional compound of the present invention is a polyfunctional compound represented by General Formula (1b).

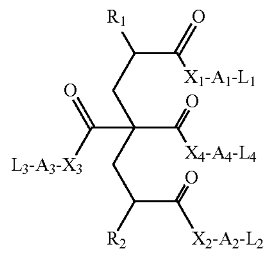

In General Formula (1b): $R_1$ and $R_2$ each independently represent any of H, $CH_3$, and Cl; $X_1$ to $X_4$ each independently represent any of —O—, —NH—, and —N(alkyl group)-; $A_1$ to $A_4$ each independently represent a divalent connecting group; and $L_1$ to $L_4$ each independently represent any of a photoisomerization group, a liquid-crystalline group, and H, and at least one of $L_1$ to $L_4$ represents a photoisomerization group or a liquid-crystalline group.

As an example of the polyfunctional compound obtained by the production method of the present invention in which $R_1$ and $R_2$ each represent $CH_3$, $X_1$ to $X_4$ each represent —O—, and $A_1$ to $A_4$ each represent an ethylene group in General Formula (1b), there is exemplified a polyfunctional compound having the following structure. The compound can be synthesized by coupling reaction of methacrylates having an azobenzene structure with malonic diester having a cyanobiphenyl structure using a hydrogen-abstraction catalyst.

One preferred embodiment of the polyfunctional compound of the present invention is a polyfunctional compound represented by General Formula (1 c).

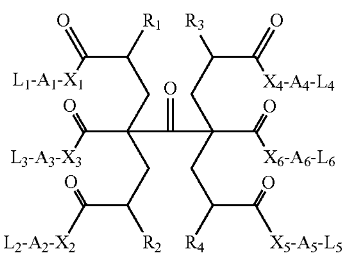

In General Formula (1c): $R_1$ to $R_4$ each independently represent any of H, $CH_3$, and Cl; $X_1$ to $X_6$ each independently represent any of —O—, —NH—, and —N(alkyl group)-; $A_1$ to $A_6$ each independently represent a divalent connecting group; and $L_1$ to $L_6$ each independently represent any of a photoisomerization group, a liquid-crystalline group, and H, and at least one of $L_1$ to $L_6$ represents a photoisomerization group or a liquid-crystalline group.

As an example of the polyfunctional compound obtained by the production method of the present invention in which $R_1$ to $R_4$ each represent H, $X_1$ to $X_6$ each represent —O—, and $A_1$ to $A_6$ each represent an ethylene group in General Formula (1c), there is exemplified a polyfunctional compound having the following structure. The compound can be synthesized by coupling reaction of acrylates having an azobenzene structure with 1,3-diethyl acetonedicarboxylate using a hydrogen-abstraction catalyst.

[Chemical Formula 12]

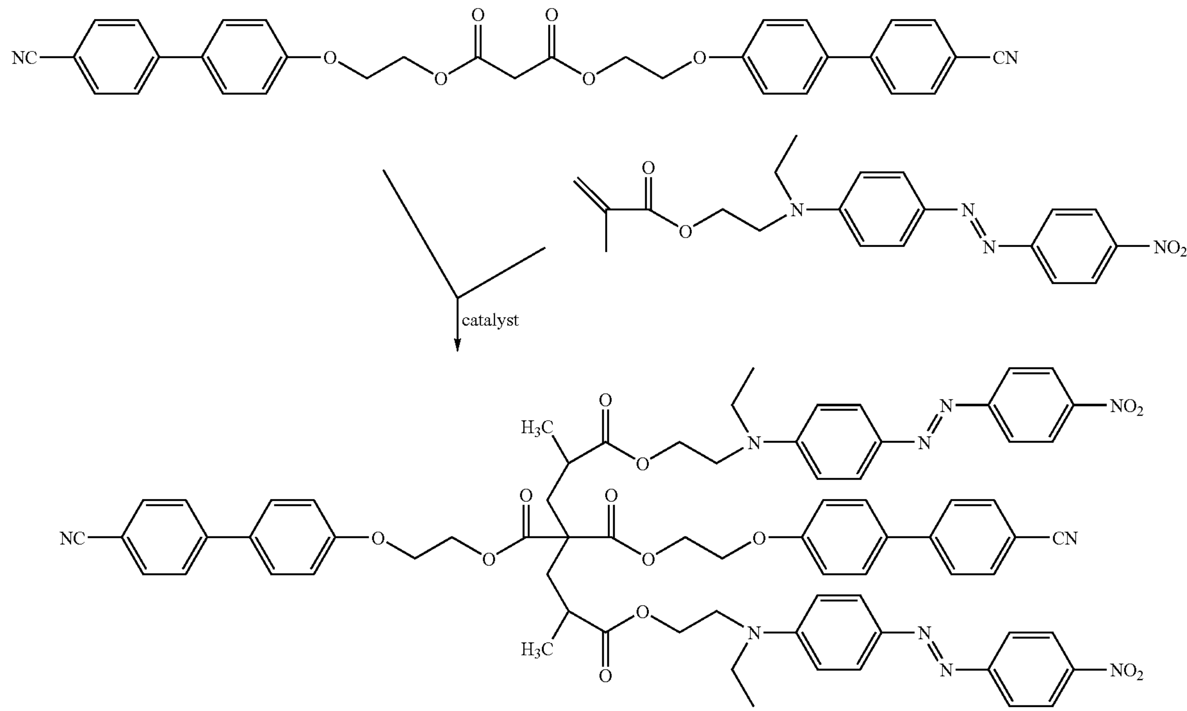

[Chemical Formula 14]

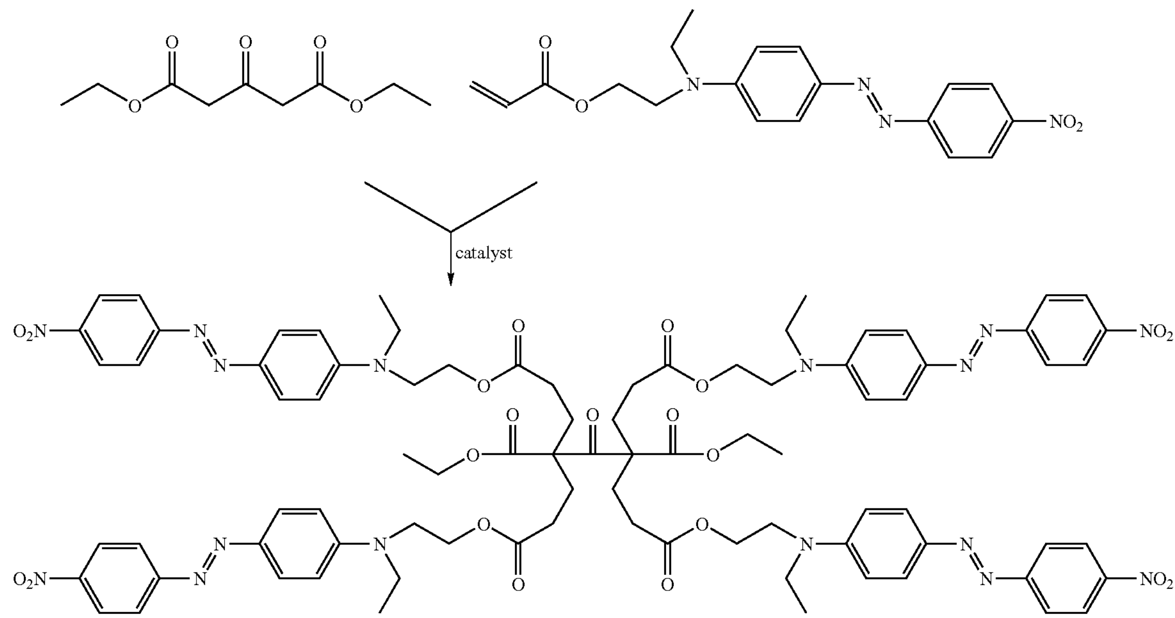

As described above, Rn (n=1 to 4) in the general formula is derived from (meth)acrylate that can be used as a raw material. Therefore, Rn can be replaced by H if acrylate is used, Rn can be replaced by $CH_3$ if methacrylate is used, and Rn can be replaced by Cl if chloroacrylate is used.

As described above, if cyanoacetates, acetoacetates, malonates, 1,3-acetonedicarboxylic acid diester, or (meth)acrylate are used as a raw material, the compound in which Xn (n=1 to 6) represents —O— in the general formula can be obtained. Further, if amide is used instead of ester, the compound in which Xn (n=1 to 6) represents —NH—, —N(alkyl)- in the general formula can be obtained.

As described above, An (n=1 to 6) and Ln (n=1 to 6) can be introduced by using raw materials having structures thereof.

It is preferred that the polyfunctional compound obtained by the production method of the present invention has a molecular weight of 500 to 5,000.

The polyfunctional compound obtained by the production method of the present invention may be used alone or in combination.

The polyfunctional compound obtained by the production method of the present invention has excellent compatibility. Therefore, it is not necessary to introduce a plurality of functional sites into one polyfunctional compound in order to express a multi-function, and an intended multi-function can be expressed by blending a plurality of polyfunctional compounds, thereby making them soluble. Further, the polyfunctional compound of the present invention has such excellent compatibility, that a film without phase separation can be obtained.

The polyfunctional compound obtained by the production method of the present invention can be used for various purposes in combination of other components. Any suitable components in accordance with purposes can be adopted as the other components. As the other components, any suitable additive can be selected appropriately within a range not impairing the effect of the present invention. Specifically, an antioxidant, a flame retardant, a leveling agent, and a plasticizer can be exemplified, and they may be used alone or in combination. Examples of the antioxidant include a phenol-based compound, an amine-based compound, an organic sulfur-based compound, and a phosphine-based compound.

<<Use of a Polyfunctional Compound Obtained by a Production Method of the Present Invention>>

The polyfunctional compound obtained by the production method of the present invention can be applied to any suitable use. For example, when the polyfunctional compound obtained by the production method of the present invention is irradiated with light, structural isomerization occurs. The structural isomerization caused by the light irradiation is a reversible reaction, and hence the light-irradiated part can be returned to an original state by heating or the like. Therefore, the polyfunctional compound can be applied to a dynamic optical function material of an optical switch or the like. Specifically, the polyfunctional compound can be used as an optical recording material on which a large quantity of data information can be optically recorded at a high density. Further, an optical recording medium or an optical recording/reproducing apparatus can also be produced using the optical recording material. Further, when the polyfunctional compound obtained by the production method of the present invention is irradiated with light, a refractive index can be modulated by the photoisomerization of a photoisomerized site, which can cause a refractive index difference between the light-irradiated part and the part not irradiated with light. Therefore, the polyfunctional compound can be applied to an optical waveguide material. Further, the polyfunctional compound obtained by the production method of the present invention can form a film, and can be used by being changed to any shape by spin coating and thermal melting. Therefore, the polyfunctional compound of the present invention can be applied to a photo-alignment film material.

EXAMPLES

Hereinafter, the present invention is described specifically by way of examples, but the present invention is not limited thereto. Unless otherwise specified, parts and percent in examples are expressed in terms of weight.

Example 1

Acrylate (2.62 g, 5.24 mmol) having a liquid-crystalline group and cyanoacetate (1.00 g, 2.62 mmol) having a Disperse Red 1 structure which was an azobenzene-based photoisomerization group were dissolved in tetrahydrofuran (30 mL) under a nitrogen atmosphere, and one drop of diazabicycloundecene (DBU) was added to the mixture, followed by stirring at room temperature for 10 minutes. 10 drops of a hydrochloric acid aqueous solution were added thereto to neutralize the reaction solution. Then, a precipitate generated when the solution was dropped to methanol was filtered. The precipitate was dissolved in tetrahydrofuran again and reprecipitated into methanol, and the precipitate was filtered and dried by heating in vacuum, whereby a polyfunctional compound (1) having one azobenzene site and two liquid crystal sites was obtained (3.00 g, 2.17 mmol, 83%).

The obtained polyfunctional compound (1) (molecular weight: 1380.4) was measured for a molecular weight by MALDI-TOFMS measurement, and as a result, only ions having m/z of 1383.5 and 1405.6 were detected. Those ions corresponded to ions in which protons were added to the polyfunctional compound (1) and ions in which sodium was added to the polyfunctional compound (1), whereby it was found that the polyfunctional compound (1) was obtained.

Example 2

Acrylate (1.64 g, 3.28 mmol) having a liquid-crystalline group and cyanoacetate (0.70 g, 1.64 mmol) having another liquid-crystalline group were dissolved in dimethylformamide (10 mL) under a nitrogen atmosphere, and one drop of diazabicycloundecene (DBU) was added to the mixture, followed by stirring at room temperature for 30 minutes. 10 drops of a hydrochloric acid aqueous solution were added thereto to neutralize the reaction solution. Then, a precipitate generated when the solution was dropped to methanol was filtered. The precipitate was dissolved in tetrahydrofuran again and reprecipitated into methanol, and the precipitate was filtered and dried by heating in vacuum, whereby a polyfunctional compound (2) having one azobenzene site and two liquid crystal sites was obtained (2.01 g, 1.41 mmol, 83%).

The obtained polyfunctional compound (2) (molecular weight: 1425.4) was measured for a molecular weight by MALDI-TOFMS measurement, and as a result, only ions having m/z of 1450.4 were detected. Those ions corresponded to ions in which sodium was added to the polyfunctional compound (2), whereby it was found that the polyfunctional compound (2) was obtained.

[Chemical Formula 15]

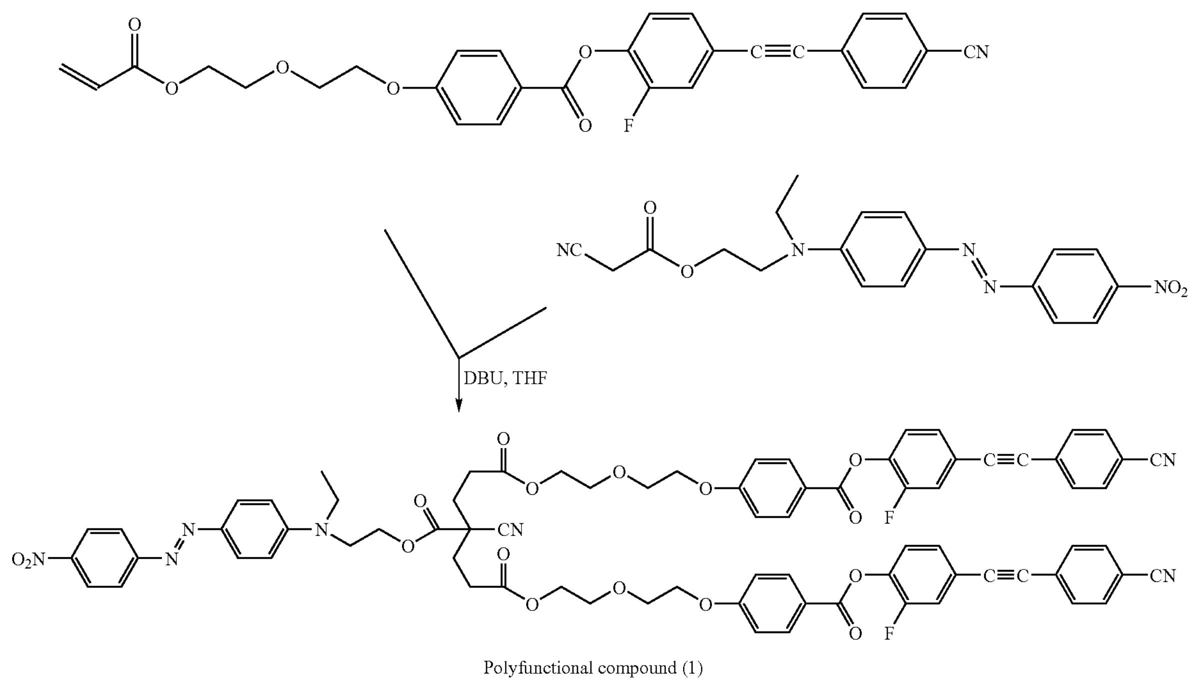

Polyfunctional compound (1)

[Chemical Formula 16]

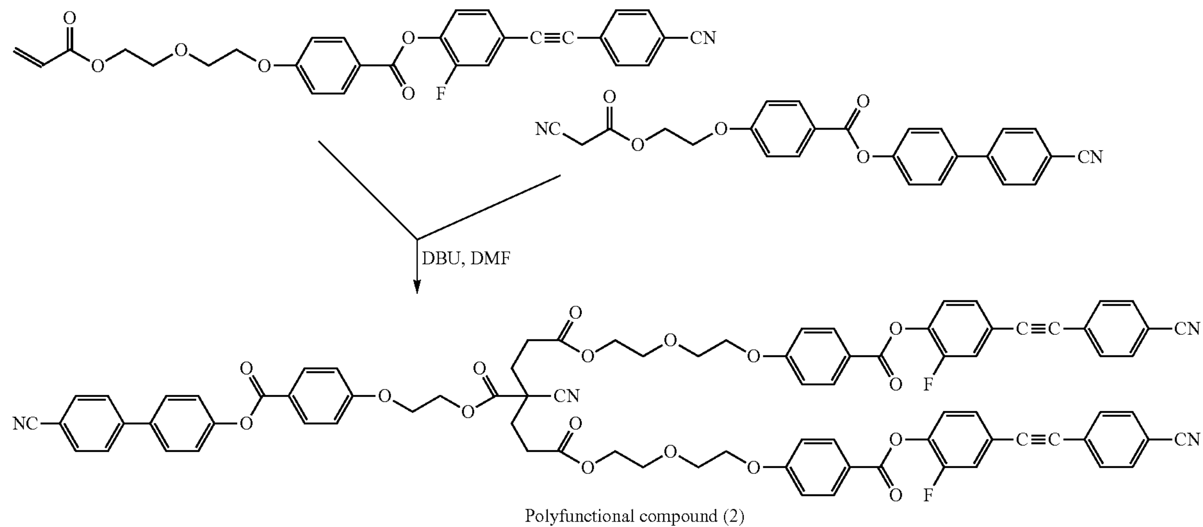

Polyfunctional compound (2)

Example 3

Cyanobiphenyl acrylate (1.38 g, 5.53 mmol) and cyanoacetate (1.00 g, 2.77 mmol) having a Disperse Red 1 structure which was an azobenzene-based photoisomerization group were dissolved in tetrahydrofuran (25 mL) under a nitrogen atmosphere, and one drop of diazabicycloundecene (DBU) was added to the mixture, followed by stirring at room temperature for 15 minutes. 10 drops of a hydrochloric acid aqueous solution were added to neutralize the reaction solution. Then, a precipitate generated when the solution was dropped to methanol was filtered. The precipitate was dissolved in tetrahydrofuran and reprecipitated into methanol, and the precipitate was filtered and dried by heating in vacuum, whereby a polyfunctional compound (3) having one azobenzene site and two liquid crystal sites was obtained (1.88 g, 2.19 mmol, 79%).

The obtained polyfunctional compound (3) (molecular weight: 879.9) was measured for a molecular weight by MALDI-TOFMS measurement, and as a result, only ions having m/z of 882.1 and 904.3 were detected. Those ions corresponded to ions in which protons were added to the polyfunctional compound (3) and ions in which sodium was added to the polyfunctional compound (3), whereby it was found that the polyfunctional compound (3) was obtained.

[Chemical Formula 17]

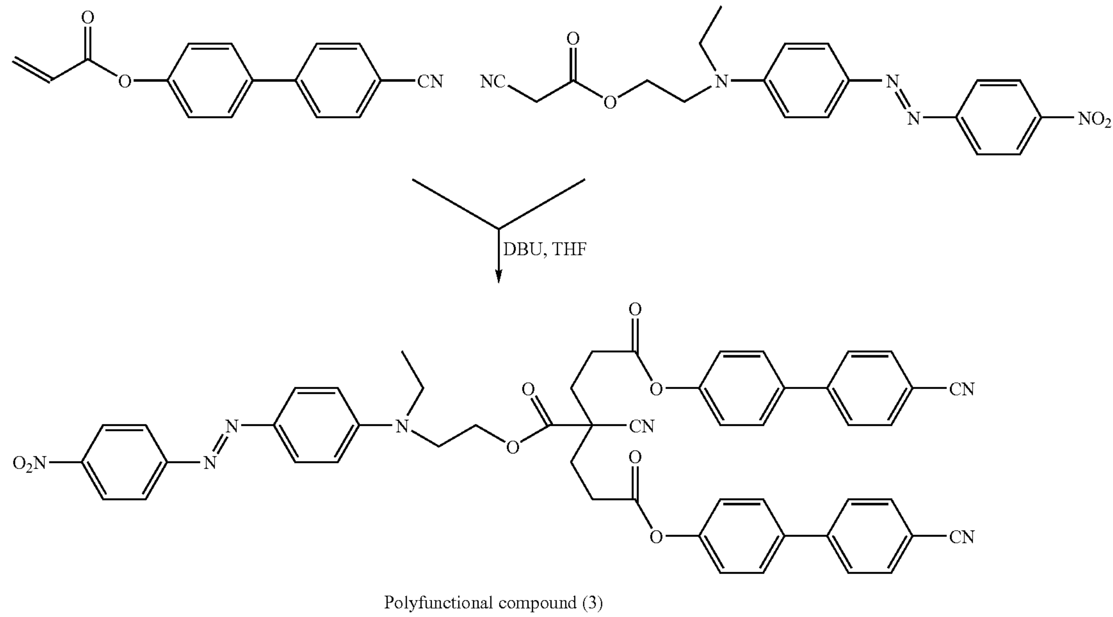

Polyfunctional compound (3)

Example 4

Acrylate (3.51 g, 14.07 mmol) having a liquid-crystalline group and cyanoacetate (3.00 g, 7.04 mmol) having another liquid-crystalline group were dissolved in dimethyl formamide (50 mL) under a nitrogen atmosphere, and two drops of diazabicycloundecene (DBU) were added to the mixture, followed by stirring at room temperature for 15 minutes. 15 drops of a hydrochloric acid aqueous solution were added to neutralize the reaction solution. Then, a precipitate generated when the solution was dropped to methanol was filtered. The precipitate was dissolved in tetrahydrofuran again and reprecipitated into methanol, and the precipitate was filtered and dried by heating in vacuum, whereby a polyfunctional compound (4) having one azobenzene site and two liquid crystal sites was obtained (6.18 g, 6.69 mmol, 95%).

The obtained polyfunctional compound (4) (molecular weight: 924.9) was measured for a molecular weight by MALDI-TOFMS measurement, and as a result, only ions having m/z of 949.9 were detected. Those ions corresponded to ions in which sodium was added to the polyfunctional compound (4), whereby it was found that the polyfunctional compound (4) was obtained.

[Chemical Formula 18]

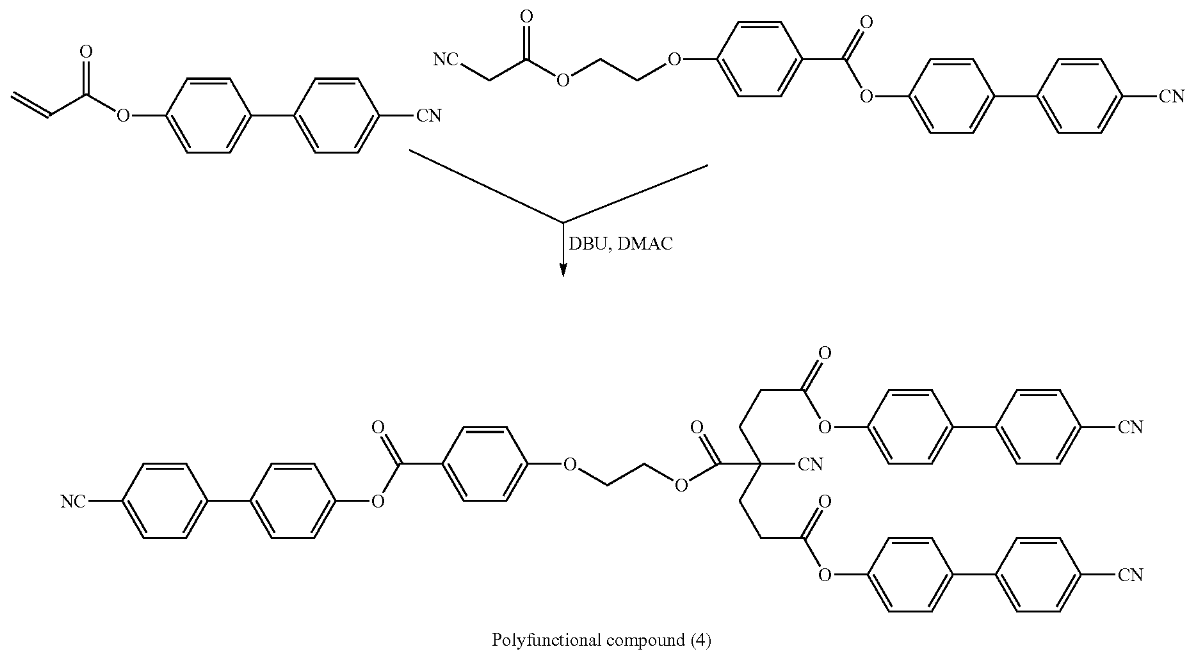

Polyfunctional compound (4)

Example 5

Malonate (0.50 g, 0.92 mmol) having two liquid-crystalline groups and methacrylate (0.73 g, 1.92 mmol) having a Disperse Red structure which was an azobenzene-based photoisomerization group were dissolved in tetrahydrofuran (25 mL) under a nitrogen atmosphere, and potassium tertiary butoxide (5 mg, 0.045 mmol) was added to the mixture, followed by stirring for 1 hour. 10 drops of a hydrochloric acid aqueous solution were added thereto to neutralize the reaction solution. Then, a precipitate generated when the solution was dropped to methanol was filtered. The precipitate was dissolved in tetrahydrofuran and reprecipitated into methanol, and the precipitate was filtered and dried by heating in vacuum, whereby red powder (0.69 g) was obtained.

The obtained compound was measured for a molecular weight by MALDI-TOFMS measurement, and as a result, ions having m/z of 929.25, 950.92, 1311.72, and 1333.03 were detected mainly. It was found that those ions corresponded to ions (theoretical value: 952) in which proton (theoretical value: 930) and sodium were added to a compound (molecular weight: 928.98) in which one molecule of azobenzene-containing methacrylate was connected to a malonate raw material having two liquid-crystalline groups, and further, corresponded to ions (theoretical value: 1334) in which proton (theoretical value 1312) and sodium were added to a compound (molecular weight: 1311.4) in which two molecules of azobenzene-containing methacrylate were connected to a malonate raw material having two liquid-crystalline groups, and thus, polyfunctional compounds (5a) and (5b) were obtained.

stirring for 3 hours. 10 drops of hydrochloric acid aqueous solution were added thereto to neutralize the reaction solution. Then, and the solution was dropped to methanol. A viscous liquid thus generated was taken out and dissolved in tetrahydrofuran. The resultant solution was reprecipitated in methanol, and the precipitate was filtered and dried by heating in vacuum, whereby red powder (0.43 g) was obtained.

The obtained compound was measured for a molecular weight by MALDI-TOFMS measurement, and as a result, ions having m/z of 813.2, 1107.2, and 1401.4 were detected mainly. Those ions corresponded to ions in which sodium

[Chemical Formula 19]

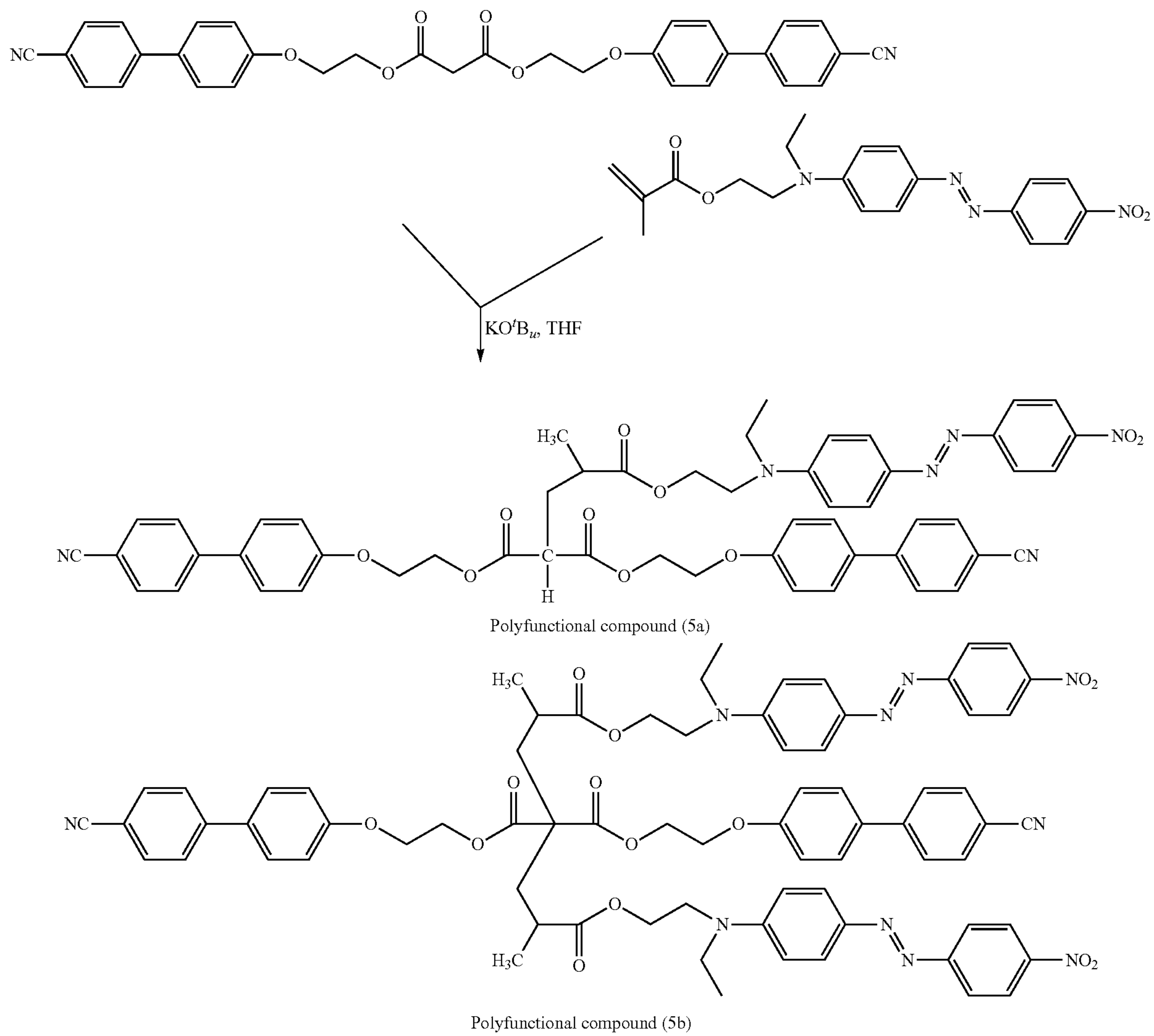

Polyfunctional compound (5a)

Polyfunctional compound (5b)

Example 6

1,3-acetonedicarboxylic acid diethyl ester (0.2585 g, 1.28 mmol) and an acrylate (1.50 g, 5.1 mmol) having a liquid-crystalline group were dissolved in tetrahydrofuran (15 mL) under a nitrogen atmosphere, and one drop of diazabicycloundecene (DBU) was added to the mixture, followed by (value obtained by adding 23 to a molecular weight) was added to a compound in which 2, 3, 4 molecules of acrylates containing liquid-crystalline groups are connected to 1,3-acetonedicarboxylic acid diethyl ester (2 adduct: 788.84, 3 adduct: 1082.15, 4 adduct: 1375.47). Thus, it was found that a polyfunctional compound (6) in which a plurality of (2 to 4) acrylates were added to 1,3-acetonedicarboxylic acid diethyl ester were obtained.

[Chemical Formula 20]

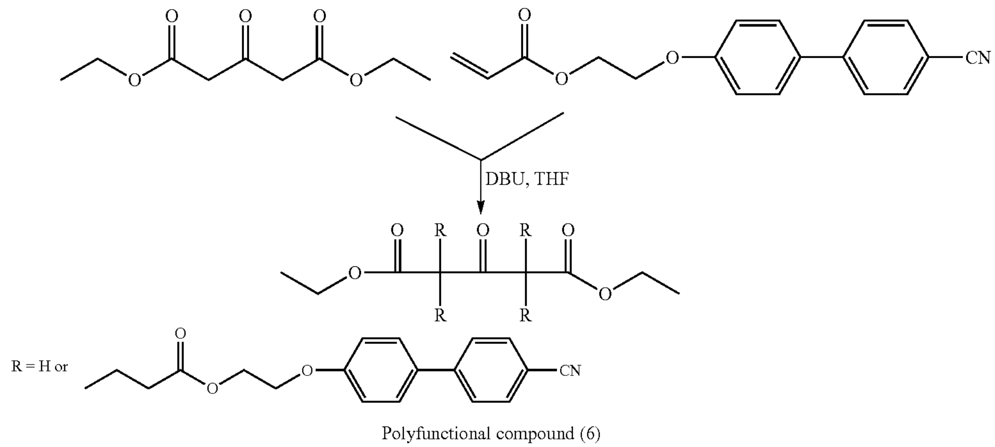

Polyfunctional compound (6)

INDUSTRIAL APPLICABILITY

The polyfunctional compound obtained by the production method of the present invention enables a material to be obtained, which controls birefringence by light irradiation to modulate a refractive index, and can be applied to optical data recording by being formed appropriately or optical elements such as a photo-alignment film, an optical waveguide material, a viewing angle compensation plate, a retardation plate, and a chloresteric reflective plate. The element thus obtained is more excellent for producing a thick film sample without any alignment defects such as phase separation, than that obtained by using a conventional polymer material, and is further excellent in optical recording characteristics (diffraction efficiency value and sensitivity in writing thereof).

The invention claimed is:

1. A method for production of a polyfunctional compound, comprising conducting a Michael addition of a compound (A) having a hydrogen atom of pKa≦15 to a (meth)acrylate or a (meth)acrylamide (B), wherein at least one of the compounds (A) and (B) has both a photoisomerization group and a liquid-crystalline group.

2. The method for production of a polyfunctional compound according to claim 1, wherein the compound (A) comprises at least one selected from cyanoacetates, acetoacetates, malonates, and 1,3-acetone-dicarboxylic acid diesters.

3. The method for production of a polyfunctional compound according to claim 2, wherein the compound (A) comprises cyanoacetates.

4. The method for production of a polyfunctional compound according to claim 1, wherein the Michael addition is performed using a hydrogen-abstraction catalyst.

5. The method for production of a polyfunctional compound according to claim 4, wherein the hydrogen-abstraction catalyst comprises a base catalyst.

6. The method for production of a polyfunctional compound according to claim 4, wherein the hydrogen-abstraction catalyst comprises an amine-based catalyst.

7. The method for production of a polyfunctional compound according to claim 1, wherein the photoisomerization group has a structure represented by General Formula (2):

(2)

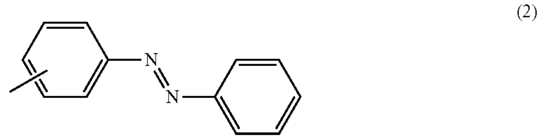

where each aromatic ring may have one or more substituents.

8. The method for production of a polyfunctional compound according to claim 1, wherein the liquid-crystalline group has a structure represented by any of General Formulae (3a) to (3g):

$$—C_y—C_y \quad (3a)$$

$$—C_y—C_y—C_y \quad (3b)$$

$$—C_y—Y—C_y \quad (3c)$$

$$—C_y—Y—C_y—Y—C_y \quad (3d)$$

$$—C_y—C{\equiv}C—C_y \quad (3e)$$

$$—C_y—C{\equiv}C—C_y—C{\equiv}C—C_y \quad (3f)$$

$$—C_y—Y—C_y—C{\equiv}C—C_y \quad (3g)$$

where: Y's represent any of —COO—, —OCO—, —CONH—, CON(alkyl)-, and —CH═N—; and Cy's each independently represent a phenyl ring, a naphthyl ring, a biphenyl ring, and a cyclohexyl ring which may have at least one substituent selected from F, CN, an alkoxy group, and an alkyl group.

9. The method for production of a polyfunctional compound according to claim 1, wherein the polyfunctional compound to be obtained has a molecular weight of 500 to 5,000.

* * * * *